United States Patent
Burke et al.

(10) Patent No.: US 10,702,401 B2
(45) Date of Patent: Jul. 7, 2020

(54) VARIABLE FRICTION-BASED SWING-PHASE CONTROLLER WITH ARTIFICIAL JOINT

(71) Applicant: LEGWORKS, INC., San Francisco, CA (US)

(72) Inventors: Brandon Burke, Stroudsburg, PA (US); Jan Andrysek, Toronto (CA)

(73) Assignee: LegWorks, Inc., Buffalo, NY (US)

( * ) Notice: Subject to any disclaimer, the term of this patent is extended or adjusted under 35 U.S.C. 154(b) by 93 days.

(21) Appl. No.: 15/094,871

(22) Filed: Apr. 8, 2016

(65) Prior Publication Data
US 2016/0296346 A1 Oct. 13, 2016

Related U.S. Application Data

(60) Provisional application No. 62/145,465, filed on Apr. 9, 2015.

(51) Int. Cl.
| | |
|---|---|
| *A61F 2/64* | (2006.01) |
| *A61F 2/62* | (2006.01) |
| *A61F 2/68* | (2006.01) |
| *F16F 7/04* | (2006.01) |
| *E05D 11/08* | (2006.01) |

(Continued)

(52) U.S. Cl.
CPC .................. *A61F 2/64* (2013.01); *A61F 2/68* (2013.01); *A61F 5/0123* (2013.01); *F16F 7/023* (2013.01); *A61F 2002/503* (2013.01); *A61F 2002/5033* (2013.01); *A61F 2002/5038* (2013.01); *A61F 2002/5039* (2013.01); *A61F 2002/5043* (2013.01); *A61F 2002/6818* (2013.01); *A61F 2002/704* (2013.01); *A61F 2002/745* (2013.01);

(Continued)

(58) Field of Classification Search
CPC ...... A61F 2005/0165; A61F 2005/0167; A61F 2005/0169; A61F 2002/6818; F16F 7/023; E05D 11/084; E05D 2011/085
USPC ............................................. 623/45; 403/120
See application file for complete search history.

(56) References Cited

U.S. PATENT DOCUMENTS

| 741,000 A | * | 10/1903 | Petre | ................ B60G 2204/416 |
| | | | | 403/120 |
| 4,685,927 A | * | 8/1987 | Haupt | ...................... A61F 2/64 |
| | | | | 623/44 |

(Continued)

FOREIGN PATENT DOCUMENTS

| GB | 1091015 | * 11/1967 | ..... A61F 2002/6818 |

OTHER PUBLICATIONS

Joshua MA, Development of a Swing-Phase Mechanism for Controlling Terminal Impact in an Artificial Knee Joint, Undergraduate Thesis Course, Department of Mechanical and Industrial Engineering University of Toronto, Mechanical & Industrial Engineering, University of Toronto, (2014) pp. 1-60.

*Primary Examiner* — David H Willse
(74) *Attorney, Agent, or Firm* — K&L Gates LLP

(57) ABSTRACT

An artificial joint with a knee axis including a swing-phase control means having a variable friction-based swing-phase controller. The variable friction-based swing-phase controller may apply different resistances at different ranges of motion by altering the torque applied upon the knee axis by altering any combination, or all of the following: the length of a lever arm and a force applied. This may be done to optimize the swing-phase control of the artificial joint to promote natural and smooth walking gait.

4 Claims, 21 Drawing Sheets

(51) Int. Cl.
*A61F 5/01* (2006.01)
*F16F 7/02* (2006.01)
A61F 2/50 (2006.01)
A61F 2/70 (2006.01)
A61F 2/74 (2006.01)

(52) U.S. Cl.
CPC ... *A61F 2002/747* (2013.01); *E05D 2011/085* (2013.01)

(56) References Cited

U.S. PATENT DOCUMENTS

| | | | | |
|---|---|---|---|---|
| 5,954,621 A * | 9/1999 | Joutras | ............... | A43B 1/0054 482/114 |
| 6,584,645 B2 * | 7/2003 | Migli | ................. | E05C 17/34 16/341 |

* cited by examiner

VARIABLE FRICTION-BASED SWING-PHASE CONTROLLER WITH ARTIFICIAL JOINT

CROSS-REFERENCE TO RELATED APPLICATIONS

This application claims priority to U.S. Provisional Patent App. No. 62/145,465 entitled "Variable Friction-Based Swing-Phase Controller with an Artificial Joint," filed on Apr. 9, 2015, the entirety of which is herein incorporated by reference.

BACKGROUND OF THE INVENTION

Unless otherwise indicated herein, the materials described in this section are not prior art to the claims in this application and are not admitted to be prior art by inclusion in this section.

Artificial joints generally require mechanisms to control their movement. For example, an artificial knee joint or a prosthetic joint will be prescribed for a person with a through-knee (TK) or an above-knee (AK) amputation (i.e., a person without a knee joint, shank, and/or foot). For a person with such an amputation, the ability for the knee to bend or articulate during sitting, kneeling, or ambulating may be desirable. It may also be desirable to have the ability to control the leg during the swing-phase of the gait when the person is walking or running, in order to prevent the heel from excessively rising off the ground and excessive terminal impact, for example. By improving control, the gait may also be improved to make the gait look more natural. Finally, the joint may need to provide sufficient support to the person in the form of stability and structural integrity. Therefore there is a need for improved joint structures and controllers.

SUMMARY OF THE INVENTION

Embodiments herein provide example mechanisms, devices, apparatuses, articles, and systems with a variable friction-based swing-phase (VFS) controller for an artificial joint.

In one example embodiment, an artificial joint comprising one or more axes to articulate at least one of a thigh portion and a shank portion around the one or more axes is disclosed. The artificial joint is attachable to the thigh portion and the shank portion. The artificial joint also includes a controller configured to vary friction associated with the articulation based at least on a degree of the articulation around the one or more axes. The varied friction may create a resistance for at least one of the thigh portion and the shank portion to articulate around the one or more axes.

In another example embodiment, an apparatus is disclosed. The apparatus may include an artificial joint that includes one or more axes. At least one of the thigh portion and the shank portion may be articulated around the one or more axes. The artificial joint may be attachable to the thigh portion and the shank portion. The apparatus may further include a controller that may be configured to vary friction associated with the articulation of the thigh portion or the shank portion based at least on a degree of the articulation around the one or more axes. The varied friction may create a resistance for at least one of the thigh portion and the shank portion to articulate around the one or more axes.

In a further example embodiment, a method is disclosed. The method may include enabling, by an artificial joint, at least one of a thigh portion and a shank portion to articulate around one or more axes of the artificial joint. The method may also include varying, by a controller of the artificial joint, a friction associated with the articulation based at least on an amount of the articulation around the one or more axes. The friction may create a resistance for at least one of the thigh portion and the shank portion to articulate around the one or more axes.

In yet a further example embodiment, an article of manufacture is disclosed. The article of manufacture may include an artificial joint comprising one or more axes. The artificial joint may be attachable between a first limb portion and a second limb portion, and may articulate at least one of the first limb portion and the second limb portion around the one or more axes. The article of manufacture may also include a controller configured to vary friction associated with the articulation based at least on an amount of the articulation around the one or more axes. The friction may be varied with a first frictional surface of the first limb portion and a second frictional surface of the second limb portion. The article of manufacture may further include one or more force applicators that may be configured to apply a force on at least one of the first frictional surface and the second frictional surface to further vary the friction based at least on the amount of the articulation around the one or more axes.

These as well as other aspects, advantages, and alternatives, will become apparent to those of ordinary skill in the art by reading the following detailed description, with reference where appropriate to the accompanying figures.

BRIEF DESCRIPTION OF THE DRAWINGS

A detailed description of the preferred embodiments is provided herein below by way of example only and with reference to the following drawings, in which.

DETAILED DESCRIPTION

Figure 1:
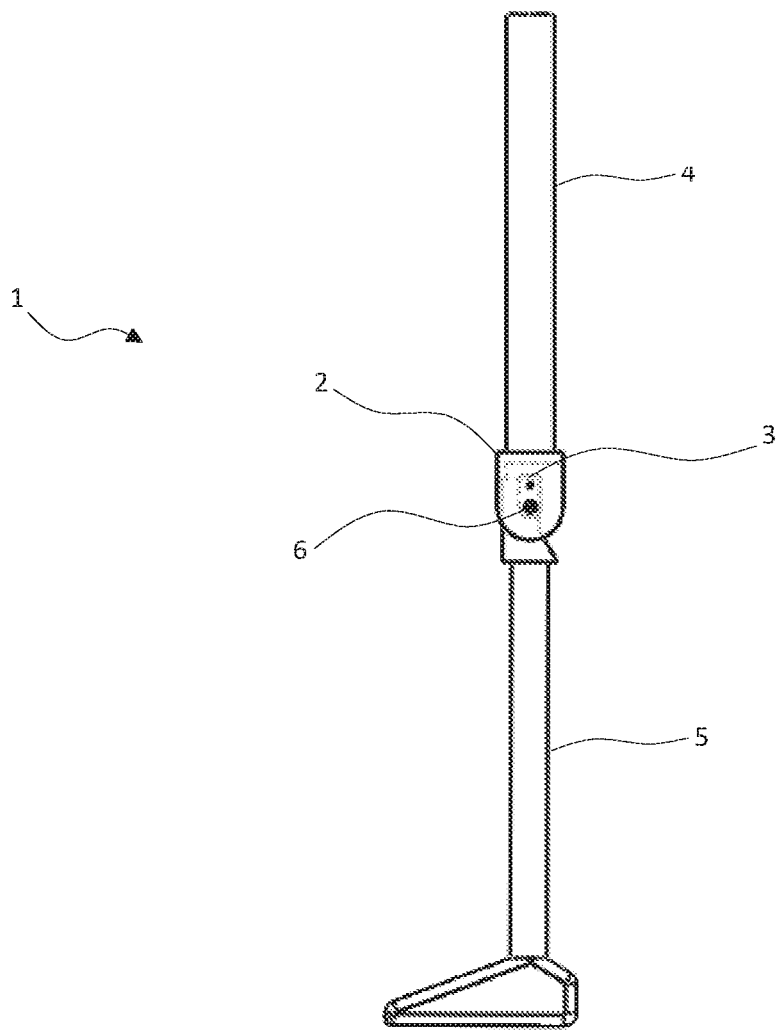
FIG. 1 is a side view of an artificial leg, in accordance with an example embodiment.

The following detailed description describes various features or operations of the disclosed mechanisms with reference to the accompanying figures. In the figures, similar symbols identify similar components, unless context dictates otherwise. The illustrative method, devices, and/or system embodiments described herein are not meant to be limiting. It may be readily understood that certain aspects of the disclosed methods, devices, apparatuses, articles of manufacture, and/or systems can be arranged and combined in a wide variety of different configurations, all of which are contemplated herein.

In one example embodiment of the present invention, an artificial leg is disclosed. The artificial leg may include a thigh portion, an artificial knee joint, and a shank portion. The artificial knee joint may include a knee axis such that the thigh portion and the shank portion may articulate or rotate around the knee axis. A VFS controller in the knee joint may be used to apply friction to resist and/or dampen the articulation or rotation around the knee axis. The control mechanism of the VFS controller may apply varying amounts of frictional resistance at different amounts or degrees of the articulation, possibly based on variable knee flexion angles. This variable amount of frictional resistance may be optimized for the knee joint by altering frictional surfaces within the VFS controller, the shape of the frictional surfaces, and/or the force applied on different areas of the frictional surfaces. The varying amount of frictional resistance may also be adjusted by tightening or loosening one or more force applicators to help fine-tune the VFS controller of the knee joint.

The VFS controller may be configured to apply a torque on the knee axis, possibly creating multiple frictional surfaces that interact with each other. For example, one frictional surface may be associated with the movements of the thigh portion of the artificial leg and the other frictional surface may be associated with the shank portion of the leg. The frictional surfaces may be directly or indirectly attached to the thigh and shank portions, as described further herein and illustrated by the accompanying figures. In a particular embodiment, the frictional surfaces may be direct in the AT-Knee, as further described herein. Further, the frictional surfaces may be indirect in hydraulic knees using linear cylinders, possibly friction-based cylinders. Contact between the surfaces may result in a frictional resistance that is dependent on the force between the surfaces, and the coefficient of friction.

Furthermore, the frictional resistance may be dependent on the relative position of the thigh portion and shank portion, such as the knee angle. The frictional resistance may be varied based on adjusting force levels at different knee flexion angles, using multiple independent adjustments, and/or by altering the geometry of the frictional surfaces, which may result in an alteration of the amount of torque applied on the joint. These force adjustments based on knee flexion angles may be implemented independently of, or in addition to, a constant friction control that may act throughout the full knee-flexion/extension cycle. Other mechanisms, such as an extension assist spring, hydraulic, and/or a pneumatic cylinder may be used to further augment the above-described swing-phase control.

Furthermore, the VFS controller may apply varying amounts of frictional resistance in the form of a torque upon the knee axis at different amounts or degrees of knee articulation, possibly based on variable knee flexion angles. The torque may be applied through altering one or more of the force applied and the lever arm length.

Variable friction-based resistance in an artificial knee joint may be achieved by altering the force applied at varying amounts or degrees of knee articulation. In particular, this may be achieved using one or more of the following methods: increasing or decreasing the respective interacting frictional surface areas (e.g., compressed by main friction control or adjustment) of the thigh portion and the shank portion, and potentially using force applicators to increase the force applied. The frictional surfaces may be compressed in the tightening of the main friction adjustment, which may result in an applied frictional force on the artificial joint. As the knee articulates and the amount of surface area increases or decreases, more or less frictional surface area may be compressed, possibly resulting in either an increase or a decrease in stiffness that respectively increases or decreases the amount of frictional force applied. Increasing or decreasing the force applied on the frictional surfaces at different amounts or degrees of articulation may also occur through increasing or decreasing the amount of interference, resulting in respectively increasing or decreasing the amount of force applied based on the similar principles stated above. Increasing interference may further compress the frictional surfaces, resulting in a greater force applied and greater frictional resistance of the artificial joint. Decreasing the interference may result in the opposite effect, and thus may decrease the frictional resistance of the artificial joint, thereby making it easier to swing the leg forward. Force applicators may also be used in the artificial joint to further increase the amount of resistance applied at certain amounts or degrees of knee articulation, and may allow the fine-tuning of the VFS controller resistance at various amounts or degrees of knee articulation. This may allow the needs of an individual to be adjusted with more than one control mechanism.

Variable friction-based resistance in an artificial knee joint may be achieved through altering the lever arm length, possibly associated with the torque applied by the frictional surfaces. This may be achieved by altering the shape of the frictional surfaces from circular, friction washers, for example, to shapes that are non-circular. Friction (which is the product of force and the coefficient of friction) may be independent of the area it is applied onto, so the distance of the lever arm may be determined by the mean distance of the frictional surface from the knee axis at variable amounts or degrees of articulation. Increasing the distance the friction material extends from the knee axis may result in an increase in the length of the lever arm, and may result in an increase of the torque caused by the frictional force, thus increasing the amount of swing-phase control resistance.

Advantages of the VFS controller with the artificial joint include having more control in the swing-phase of the joint than other joints (e.g., constant friction knee joints), among various other phases of the gait. Further, the controller may be a lighter-weight, more compact, and lower costing controller than hydraulic or pneumatic knees, while creating efficiency and a natural appearance of the gait for the user that can be used in a variety of applications such as prosthetic, orthotic, and/or robotic applications.

As contemplated herein, a gait may have a number of phases. For example, the swing phase of the gait may correspond to a phase in which a prosthetic leg lifts off the ground behind the user and swings forward to a position on the ground in front of the user. The "swing-phase control" may refer to the control of the movement or articulation of the joint during the swing-phase of the gait cycle to make the gait efficient and also a natural appearance of the gait. In some instances, friction, pneumatics and/or hydraulics may be used to resist or dampen the movement or articulation of the knee joint to help control aspects of the swing-phase. Increasing the resistance or damping at the knee joint may slow the relative movement or articulation between the thigh and shank portions of the leg. Yet further, decreasing resistance or damping at the knee joint can increase the relative movement or speed up the relative movement between the thigh and shank portions of the leg, for example. In some instances, a variable friction-based swing-phase (VFS) controller, described herein, may allow the resistance to be increased or decreased as required or preferred by a given prosthetic user.

In some instances, the VFS controller may provide varying levels of resistance to further improve the gait of users. In particular, the VFS controller may be configured to apply different or variable amounts of resistance at different phases or parts of the gait cycle. For example, some controllers may take the form of hydraulic and/or pneumatic controllers. In such examples, it may be preferred to have relatively low resistance at the beginning of swing-phase of gait as the knee begins to flex, followed by increased resistance to prevent excessive knee flexion and the heel excessively rising off of the ground. Once the full knee is flexed, e.g., where knee flexion is achieved, knee extension commences. Resistance may initially be low to allow for knee extension, and may then increase as the weight of the user shifts on to the knee and the knee approaches full extension to slow movement and prevent terminal impact or hyperextension. Hydraulic and pneumatic dampers may be designed with the controller to provide variable damping throughout the knee flexion and extension cycle, as described above. Thus, such dampers may be used to facilitate the desired movements during gait.

In some instances, various challenges associated with designing artificial joints, such as the complexity involved in the designs, the costs associated with the designs, and the designs being prone to leaks and failures, may be overcome. For example, a VFS controller may have a simple design, the controller may be cheaper, and the controller may be easier to maintain and repair. However, one design challenge may be related to the controller providing adequate control over the swing-phase and having the ability to provide variable resistance at different stages of swing-phase. In particular, as opposed to providing only constant friction and/or resistance, it may be desirable or necessary to have the variable resistance at different stages of the swing-phase.

Therefore, in view of pneumatic or hydraulic systems, some friction systems may operate without effective swing-phase control and may result in a lack of movements necessary to create a natural appearance of the gait, suffering from the heel excessively rising off of the ground, terminal impact, and elongated swing-phase duration. Artificial joints without VFS controllers may have disadvantages similar or different from those of hydraulic and pneumatic swing-phase controllers described herein. For example, some controllers may include continuous friction and multiple friction brake mechanisms configured to be engaged at various stages of a swing-phase to more closely replicate the human function of the quadriceps and hamstring muscles. Systems including such controllers may include various complexities, particularly with many parts such as brakes or multiple braking mechanisms superimposed. Such systems may be embodied with separate frictional forces applied with individual applicators to various frictional materials superimposed at certain ranges of motion over a continuous friction application. Surface area changes to the friction brakes may be limited to improving durability without further applying additional frictional force. The multiple constant frictional forces applied may function to create a net variable friction effect; however, such an effect may lack smooth transitions from one level of resistance to another. Such mechanisms may also impose a range of motion stops, which can negatively affect an ability of an amputee to sit or stand comfortably. Notably, it is also unknown whether such mechanisms have led to an artificial joint available in the market, as it is currently not available in the market, despite the fact that constant friction artificial joints continue to exist and be used, despite being less functional.

The variable friction-based swing-phase (VFS) controller with an artificial joint may control the swing-phase of the joint through a large or full range of motion. The VFS controller may be simpler, light-weight, compact, and thereby cheaper to manufacture. The VFS controller may also produce an efficient gait and a natural appearance of the gait based on having smoother transitions with variable swing-phase control resistance and a variable friction mechanism that can be used in numerous other applications, such as orthotic and robotic applications. Further, the VFS controller may decrease wear on other components and materials in the artificial joint, and further without interfering with the stance-phase mechanism of the artificial joint.

All elements described below may be switched or interchanged between thigh portion and the shank. For example, friction surfaces, e.g., friction shims, may be attached to either the thigh portion or the shank portion. Also, while the below descriptions demonstrate a mechanism whereby the VFS controller is integrated directly within the shank and thigh portions of the knee, additional embodiments may considered. For example, friction to the knee joint can be applied using additional linkages that connect to a mechanism capable of applying frictional resistance.

Figure 2:
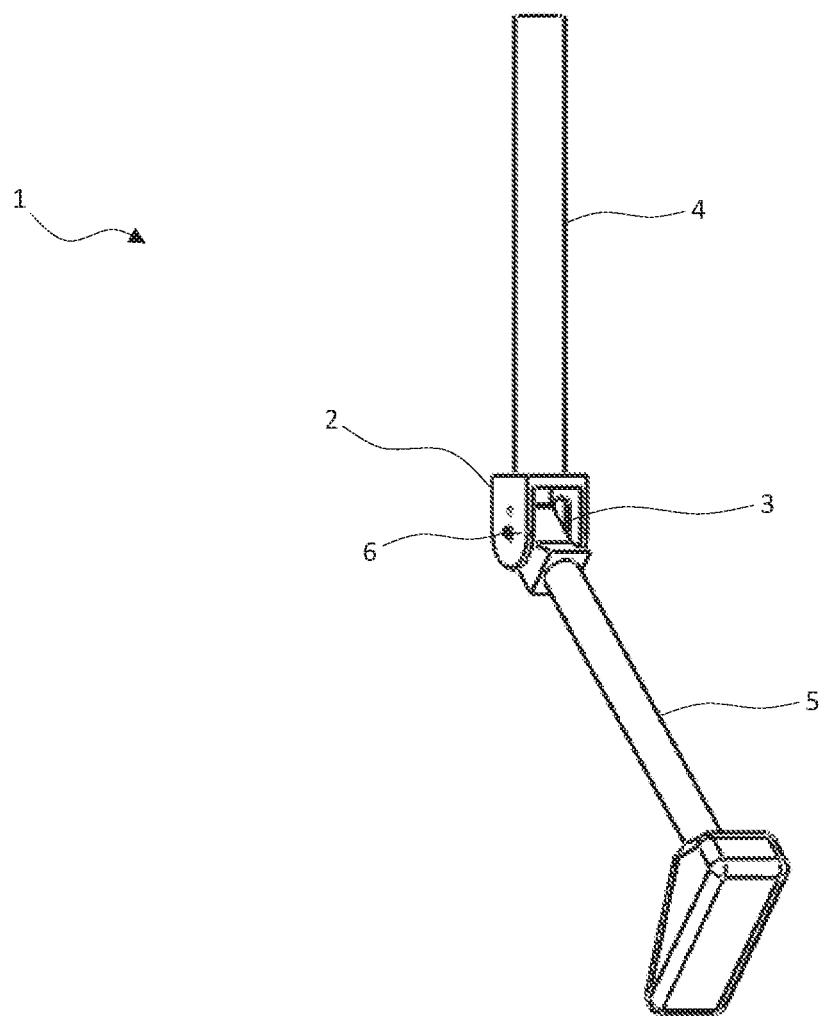
FIG. 2 is a perspective view of the artificial leg of FIG. 1 and a knee joint with a knee axis, in accordance with an example embodiment.

Referring to FIGS. 1 and 2, provided are side and perspective views, respectively, of an artificial leg 1, in accordance with an example embodiment. As shown, the artificial leg 1 includes an artificial knee joint 2 and a variable friction-based swing-phase (VFS) controller 3 in relation to a thigh portion 4 and a shank portion 5. The knee joint 2 further includes a knee axis 6 (which may include one or more axes), in which the thigh portion 4 and the shank portion 5 may articulate around. It is noted that the knee axis 6 may be an instantaneous center of the knee joint 2, such as in the case of multi-bar linkage mechanisms of polycentric knee joints. The VFS controller 3 may apply resistance to the thigh portion 4 and/or the shank portion 5 based on the articulation around knee axis 6.

Figure 3:
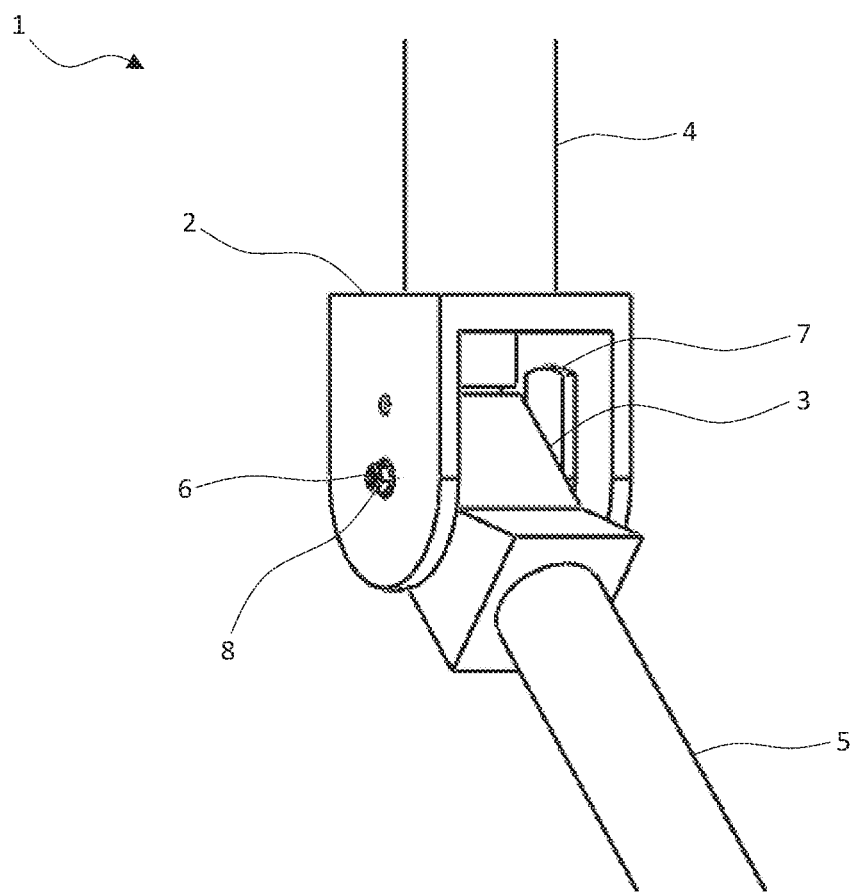
FIG. 3 is a closer, perspective view of the knee joint and a variable friction-based swing-phase (VFS) controller, in accordance with an example embodiment.
Figure 4:
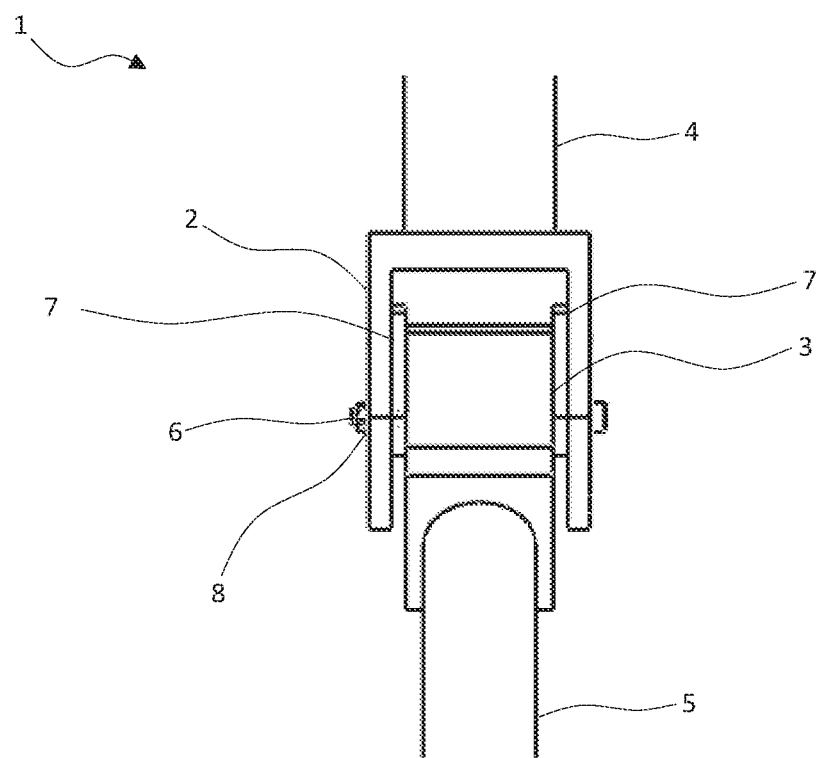
FIG. 4 is a rear view of the knee joint of FIG. 2 and the VFS controller of FIG. 3, in accordance with an example embodiment.

FIG. 3 is a closer, perspective view of the knee joint 2 and VFS controller 3, in accordance with an example embodiment. FIG. 4 is a rear view of knee joint 2 of FIG. 2 and the VFS controller 3 of FIG. 3, in accordance with an example embodiment. Further, as shown in FIG. 4, the VFS controller 3 includes friction shims 7 and a friction control screw 8. Friction shims 7 and friction control screw 8 may apply friction-based resistance to control the articulation of knee joint 2 around knee axis 6. Friction shims 7 may be attached to the thigh portion 4 to slide against a frictional surface on shank portion 5. Friction control screw 8 may apply an axial force through or around the knee axis 6, which may compress the thigh portion 4, shank portion 5, and friction shims 7, resulting in an applied frictional force that acts as resistance to the articulation of knee joint 2 during swing-phase. This may thereby enable the user to control the articulation.

Figure 5:
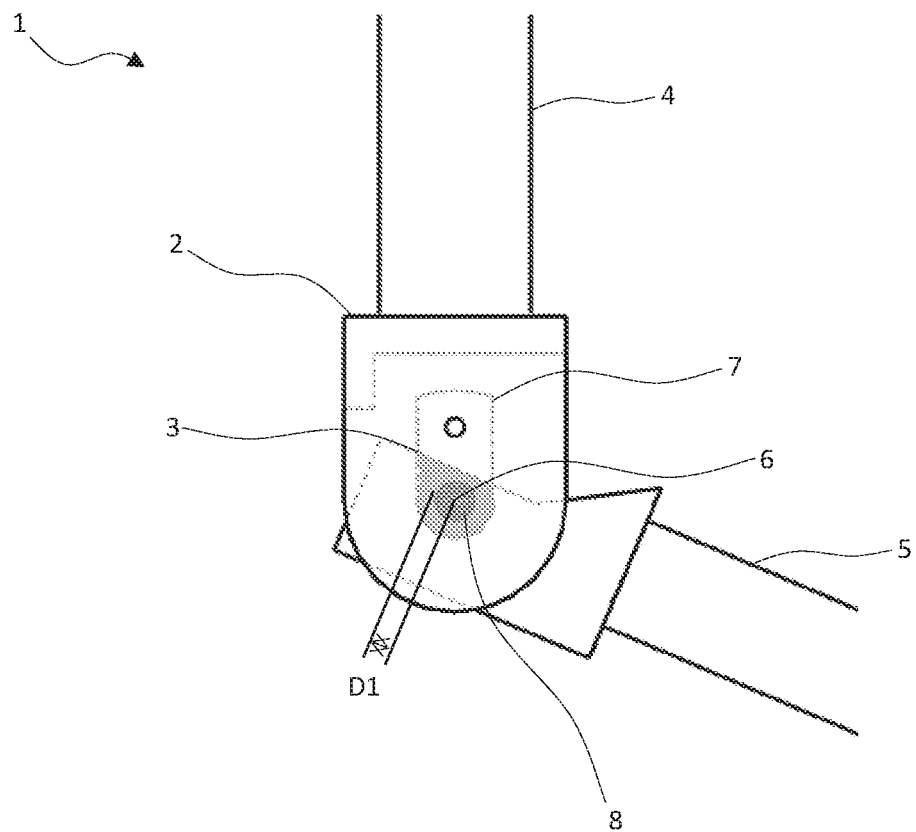
FIGS. 5 and 6 are operational side views of the knee joint of FIGS. 1-4, including the VFS controller of FIG. 3, in accordance with an example embodiment.
Figure 6:
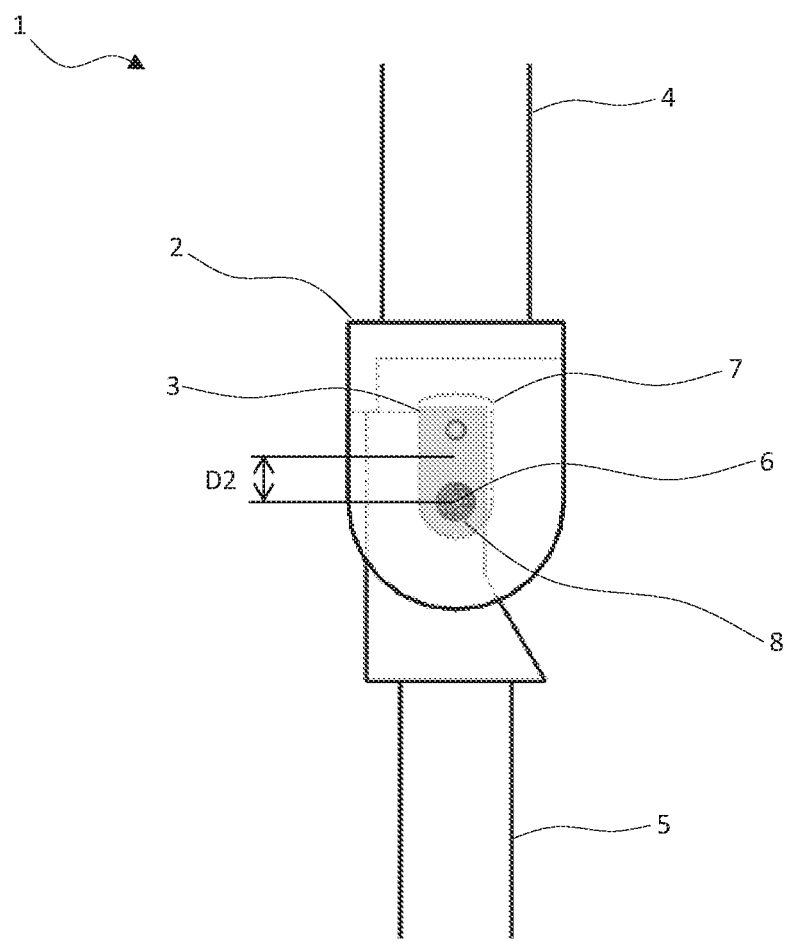

FIGS. 5 and 6 are operational side views of the knee joint 2 of FIGS. 1-4, including the VFS controller 3 of FIG. 3, in accordance with an example embodiment. FIG. 5 illustrates the knee joint 2 in a flexed position around knee axis 6, where the thigh portion 4 or the shank portion 5 articulates around the knee axis 6. FIG. 6 illustrates knee joint 2 in an extended, straight position, possibly such that the knee joint 2 is in a fully extended, straight position. Friction shims 7 and the shank portion 5 are shown to both be non-circular in shape. The overlapping portions of the friction shims 7 and the shank portion 5 in FIGS. 5 and 6 are shaded gray to illustrate that as knee joint 2 articulates around knee axis 6, the shape and the amount of respective overlapping surface areas of friction shims 7 and shank portion 5 changes accordingly. The respective overlapping and/or interacting surface areas of the friction shim 7 and shank portion 5 apply the frictional resistance that controls the articulation of knee joint 2 around knee axis 6 in the swing-phase of the gait. Further, the change in both the shape and the surface area of the respective overlapping and/or interacting surface areas of the friction shims 7 and shank portion 5 changes the amount of resistance in the swing-phase. Various changes to the shape and/or the respective overlapping and/or interacting surface areas may be implemented to vary the friction-based control. Primary principles that are involved in the VFS controller 3 include Friction≡force×friction coefficient and Torque≡force×distance.

As shown in FIGS. 5-6, the respective interacting frictional surfaces of friction shims 7 and the shank portion 5 illustrates that as the knee articulates, one or more dimensions of the respective interacting surfaces may change. For example, the length of the respective interacting surfaces may change, possibly including the length of the lever arm. As the respective interacting surface areas changes and the mean distance D1 (shown in FIG. 5) of the respective interacting surfaces from the knee axis 6 increases from D1 to D2 (shown in FIG. 6), the length of the lever arm also increases, resulting in a subsequent increase in torque applying resistance to the swing-phase control of the knee joint 2. Decreasing the mean distance from D2 to D1 of the respective interacting surfaces decreases the length of the lever arm, resulting in a subsequent decrease in torque applying resistance to the swing-phase control of knee joint 2. Variable friction-based swing-phase control in this manner may be used as the prominent variable of the amount of friction, possibly being one or more of the only variables that apply the resistance. Variable friction-based swing-phase control in this manner may also be used in conjunction with a subsequent change in the amount of the respective interacting surface areas of friction shims 7 and shank portion 5, as illustrated in this preferred embodiment.

In some embodiments, frictional force may be independent of the amount of surface area the force is applied through. For example, the change in the respective interacting surface areas of the friction shims 7 and shank portion 5 of knee joint 2 may result in a change of the force applied to the interacting surface areas, without the use of force applicators. As such, this may result in a change in the amount of resistance for the thigh portion 4 and/or the shank portion 5 to articulate around the one or more knee axes 6. As noted, the friction control screw 8 may be a mechanism for compressing the thigh portion 4, the shank portion 5, and the friction shims 7, possibly resulting in a force being applied or created on the respective interacting surfaces, such that the resistance controls the articulation of knee joint 2. Solids have elastomeric properties that may be compressible with more compressed solids being stiffer than their less compressed solids or versions. As the respective interacting surface areas of the friction shims 7 and the shank portion 5 changes, the compression force applied through friction control screw 8 may also subsequently change. This change in the compression alters the force applied through thigh portion 4, the friction shims 7, and the shank portion 5.

In practice, changes in the percentage of respective interacting surface areas applying the frictional resistance from the total surface area may cause a change in the amount of frictional resistance by the same percentage. In practice, there may be a small counteraction of the elongation, possibly based on the friction control screw 8 described above in relation to FIGS. 3-4. The elongation may be based on various properties of the friction control screw 8, such as the friction control screw 8 being a solid with elastomeric properties or a much stiffer material, so the elongation would be negligible. In some instances, the respective interacting surface areas of the friction shims 7 and the shank portion 5 may be altered. Further, the respective interacting surface areas may be altered or changed prior to use, during uses, and/or subsequently after uses. In particular, the alterations may be made to the shape of the respective interacting surfaces, the dimensions (e.g., the length, width, and/or thickness) of the surfaces, and/or the compositions of the surfaces, among other properties of the surfaces contemplated herein.

Figure 7:
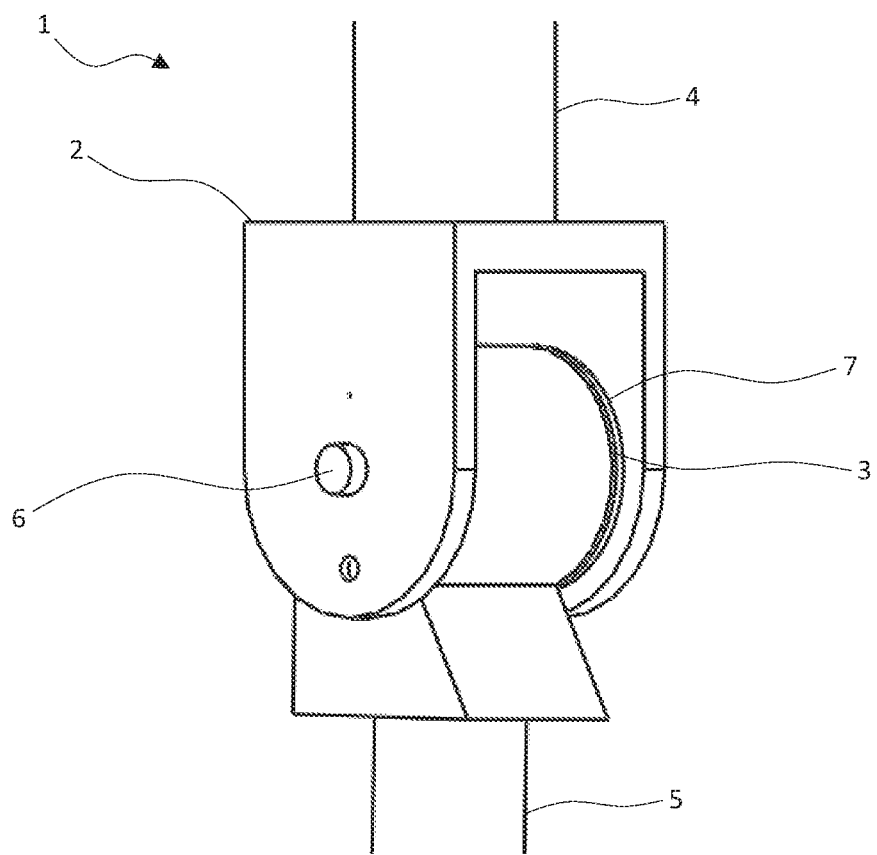
FIG. 7 is an exploded, perspective view of the knee joint of FIGS. 2 and 3 and the VFS controller, in accordance with an example embodiment.

FIG. 7 is a perspective view of the knee joint 2 of FIGS. 2 and 3 including the VFS controller 3, as described above in accordance with an example embodiment. As shown, the artificial leg 1 described above in relation to FIGS. 1-6 includes one or more axes 6 to articulate the thigh portion 4 and/or the shank portion 5 around the one or more axes 6. Further, as illustrated, the artificial leg 1 is attachable to the thigh portion 4 and the shank portion 5. Notably, the VFS controller 3 is configured to vary friction associated with the articulation based on a degree of the articulation around the one or more axes 6. As described, the varied friction may create a resistance for the thigh portion 4 and/or the shank portion 5 to articulate around the one or more axes 6. As shown, the varied friction may create a particular resistance based on the corresponding knee flexion angle, such as where the knee is extended.

Figure 8:
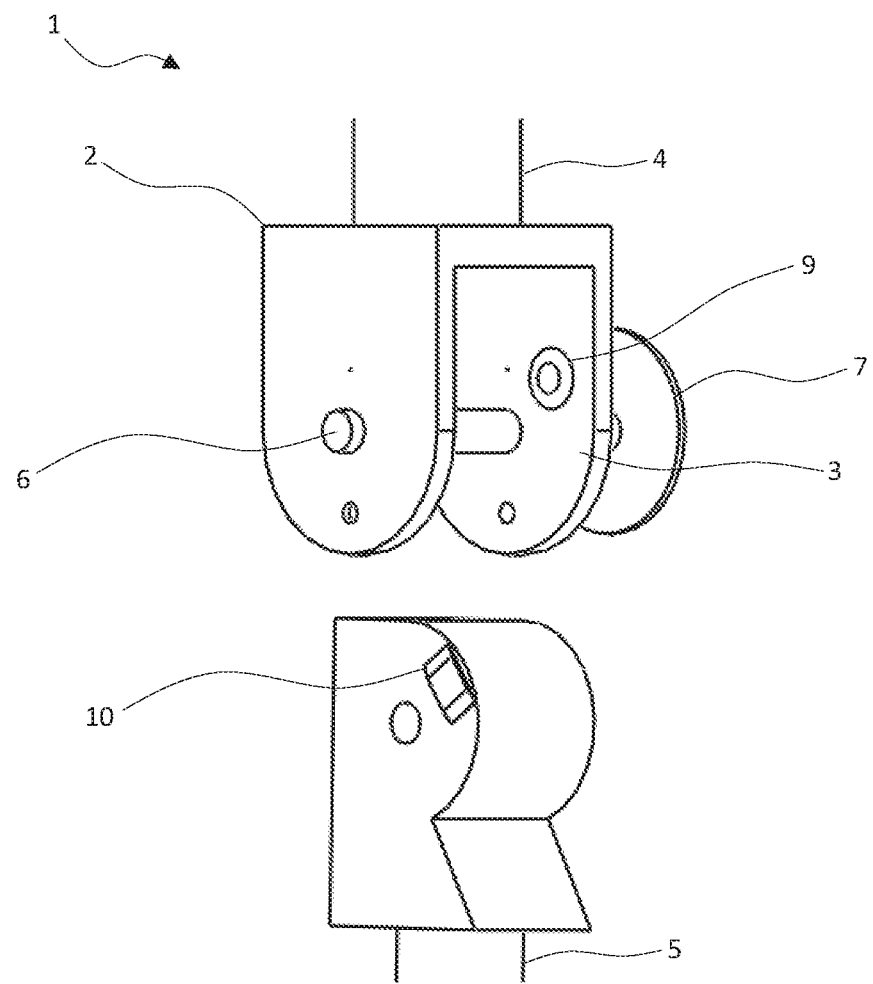
FIG. 8 is an exploded view of the knee joint from FIG. 7 with force applicators, in accordance with an example embodiment.

FIG. 8 is an exploded view of the knee joint 2 from FIG. 7 with force applicators 9 and 10, in accordance with an example embodiment. As shown, FIG. 8 illustrates the friction shims 7, a force applicator 9 of the thigh portion 4, and a force applicator 10 of the shank portion 5. The force applicators 9 and 10 may apply respective forces to increase one or more amounts of interference on various portions of the artificial joint. For example, referring back to FIGS. 3-4, the interference may be applied on the friction control screw 8 described above to increase the amount of frictional resistance applied to control swing-phase. In particular, a number of components of the artificial leg 1 may be compressed together including: the thigh portion 4, the shank portion 5, the friction shims 7, the force-applicator 9, and the force applicator 10. As such, the compression may increase the amount of frictional resistance to control various phases of the gait.

Figure 9:
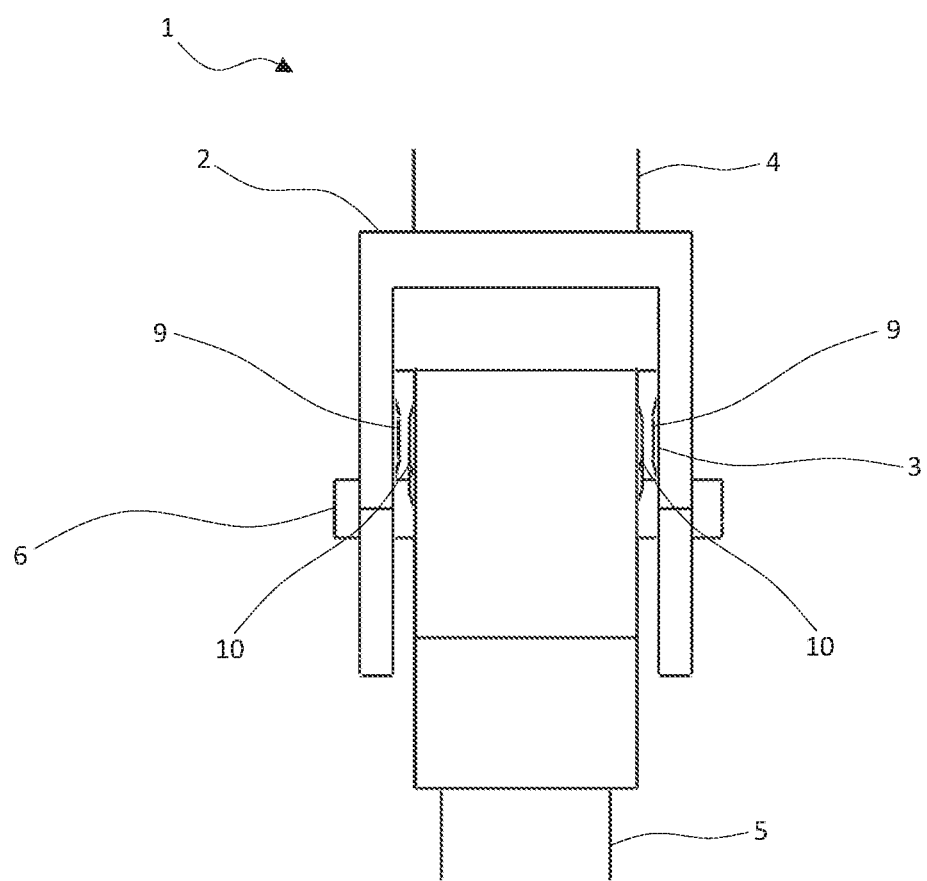
FIG. 9 is a rear view of the knee joint of FIG. 8, in accordance with an example embodiment.

FIG. 9 is a rear view of the knee joint 2 of FIG. 8, in accordance with an example embodiment. As shown, the knee joint 2 may articulate without the friction shims 7. Further, the knee joint 2 may articulate with force applicator 9 of the thigh portion 4 and applicator 10 of the shank portion 5. As shown, the artificial joint 2 includes one or more axes 6, where the artificial joint 2 is attachable between a first limb portion 4 and a second limb portion 5, to articulate the first limb portion 4 and the second limb portion 5 around the one or more axes 6. Further, the VFS controller 3 may be configured to vary friction associated with the articulation based on an amount of the articulation around the one or more axes 6. In particular, the friction may be varied with a first frictional surface of the first limb portion 4 and a second frictional surface of the second limb portion 5. As such, one or more force applicators 9 and 10 may be configured to apply a force on the first frictional surface and/or the second frictional surface to further vary the friction based on the amount of the articulation around the one or more axes 6.

Figure 10:
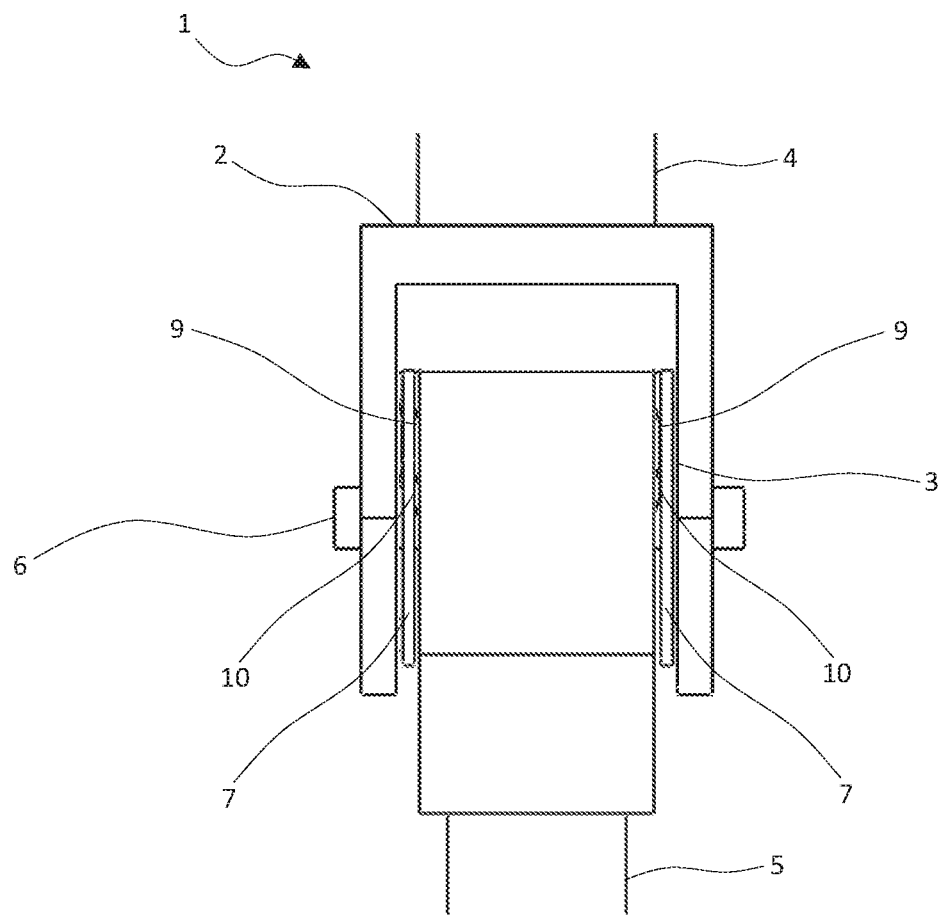
FIG. 10 is a rear view of the knee joint of FIG. 9 with the friction shims of FIG. 7 and the force applicators of FIG. 8, in accordance with an example embodiment.

FIG. 10 is a rear view of the knee joint 2 from FIG. 9 with the friction shims 7 of FIG. 7 and the force applicators 9 and 10 of FIG. 8, in accordance with an example embodiment. As shown, the knee joint 2 may include the friction shims 7. As shown, the artificial joint 2 includes the one or more axes 6, where the artificial joint 2 is attachable between a first limb portion 4 and a second limb portion 5, to articulate the first limb portion 4 and the second limb portion 5 around the one or more axes 6. Further, the VFS controller 3 may be configured to vary friction associated with the articulation based on an amount of the articulation around the one or more axes 6. In particular, the friction may vary with a first frictional surface of the first limb portion 4 (e.g., the friction shims 7) and a second frictional surface of the second limb portion 5. As such, one or more force applicators 9 and 10 may be configured to apply a force on the first frictional surface and/or the second frictional surface to further vary the friction based on the amount of the articulation around the one or more axes 6.

Figure 11:
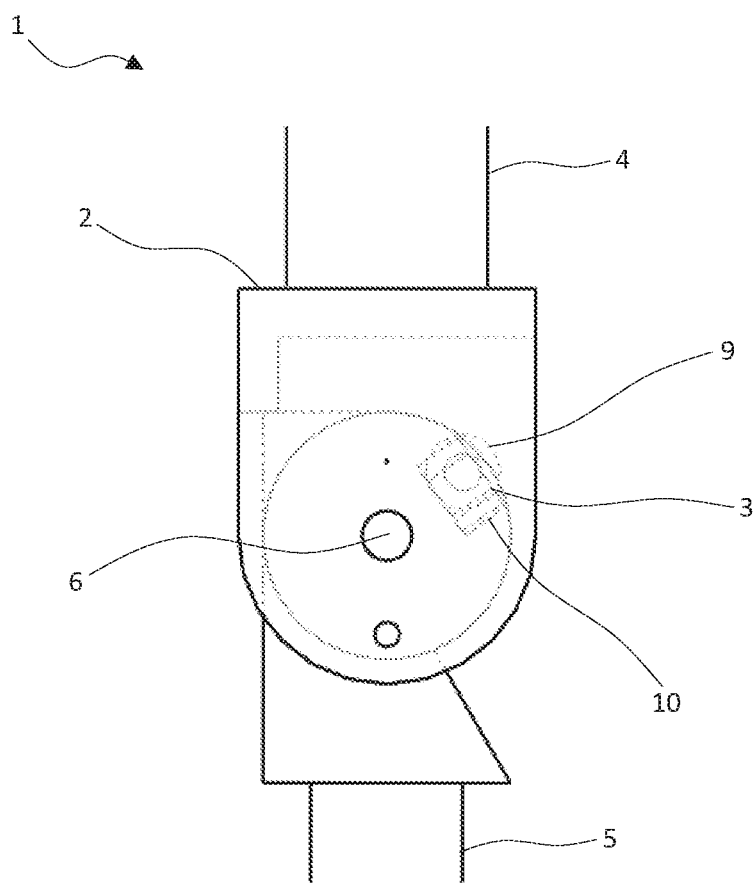
FIGS. 11 and 12 are side views of the knee joint of FIGS. 9 and 10 illustrating variable amounts of interference that may change with variable degrees of knee flexion, in accordance with an example embodiment.
Figure 12:
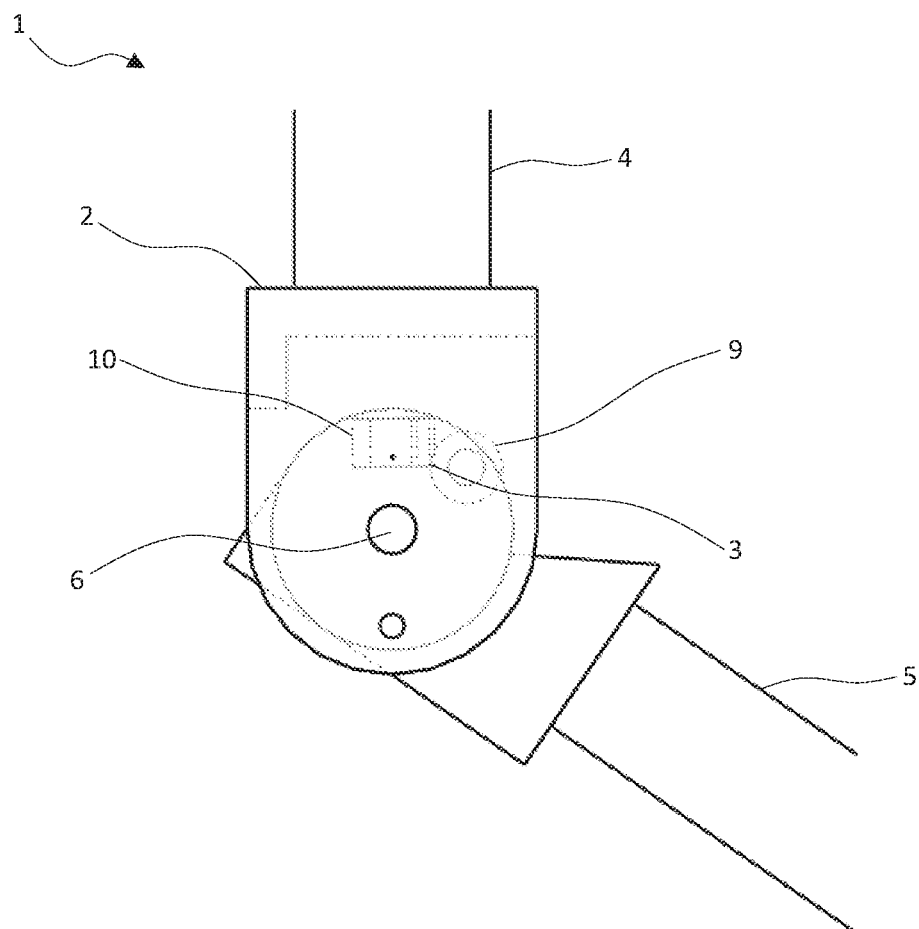

FIGS. 11 and 12 are side views of the knee joint 2 of FIGS. 9 and 10 illustrating variable amounts of interference that may change with variable degrees of knee flexion, in accordance with an example embodiment. FIG. 11 illustrates knee joint 2 in a fully extended (straight) position. FIG. 12 illustrates knee joint 2 in one or more flexed positions around knee axis 6. Further, as shown in FIG. 11, the force applicator 9 and force applicator 10 may overlap, which may indicate an increase in interference. As such, the interference may cause an increase in force that causes frictional resistance or an increase in the frictional resistance to the swing-phase of knee joint 2. Further, as shown in FIG. 12, the force applicator 9 and the force applicator 10 may not be overlapping, resulting in a decrease of frictional resistance to the swing-phase of knee joint 2 relative to FIG. 11. Various sizes, shapes, gradients, and locations of the force applicator 9 and 10 can all be adjusted to optimize the design of the VFS controller 3 to create a natural appearance of the gait.

Figure 13:
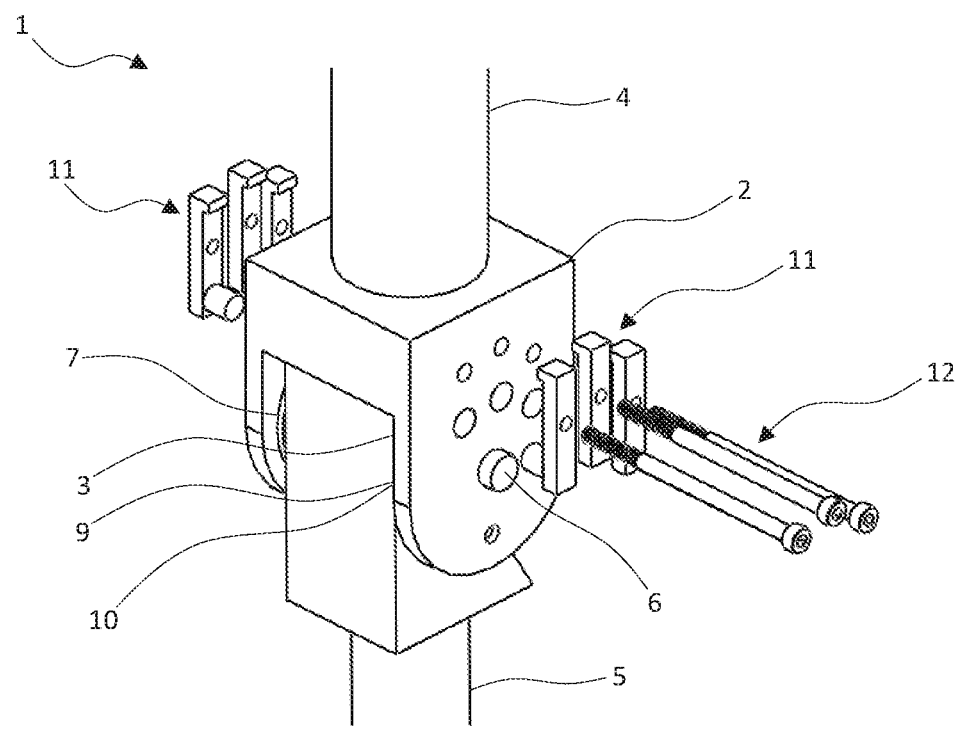
FIG. 13 is an exploded view of the VFS controller of the knee joint of FIGS. 11 and 12 with force applicators, in accordance with an example embodiment.
Figure 14:
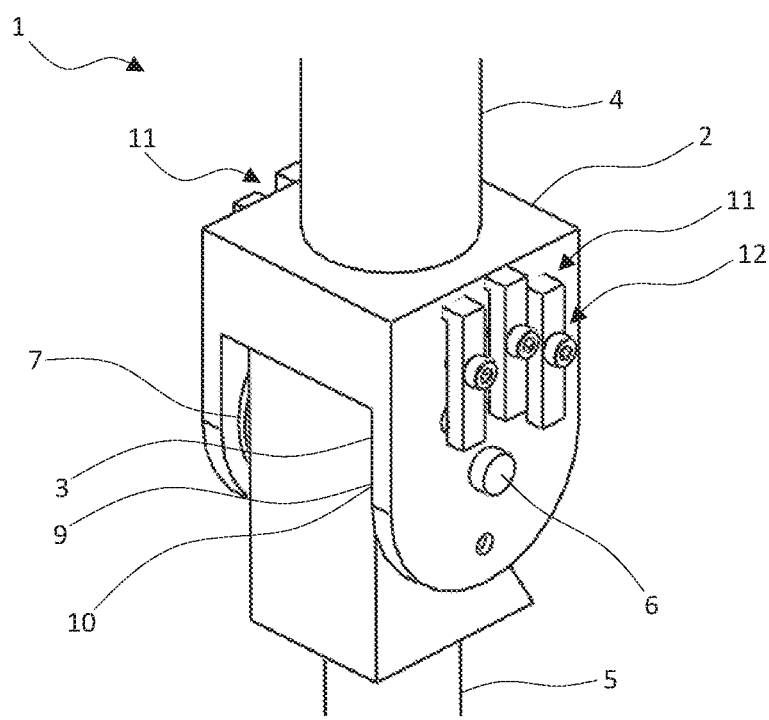
FIG. 14 is a perspective view of the VFS controller of the knee joint of FIG. 13, in accordance with an example embodiment.

FIG. 13 is an exploded view of the VFS controller 3 of the knee joint 2 of FIGS. 11 and 12 with the force applicators 9 and 10, in accordance with an example embodiment. FIG. 14 is a perspective view of the VFS controller 3 of the knee joint 2 of FIG. 13, in accordance with an example embodiment. As shown, force applicator arms 11 may be attached to the knee joint 2 with the friction control screws 12. The friction control screws 12 may apply force through force applicator arms 11 and onto the friction shims 7, thereby increasing interference. As such, the increased interference may result in an increased resistance of the swing-phase of the knee joint 2. The force applicator arms 11 may be arranged to optimize the desired swing-phase control based on the location of the increased interference. Furthermore, the friction control screws 12 allow for the customization of the amount of interference at different amounts of articulation or knee flexion, adjusting the swing-phase resistance for knee joint 2.

Figure 15:
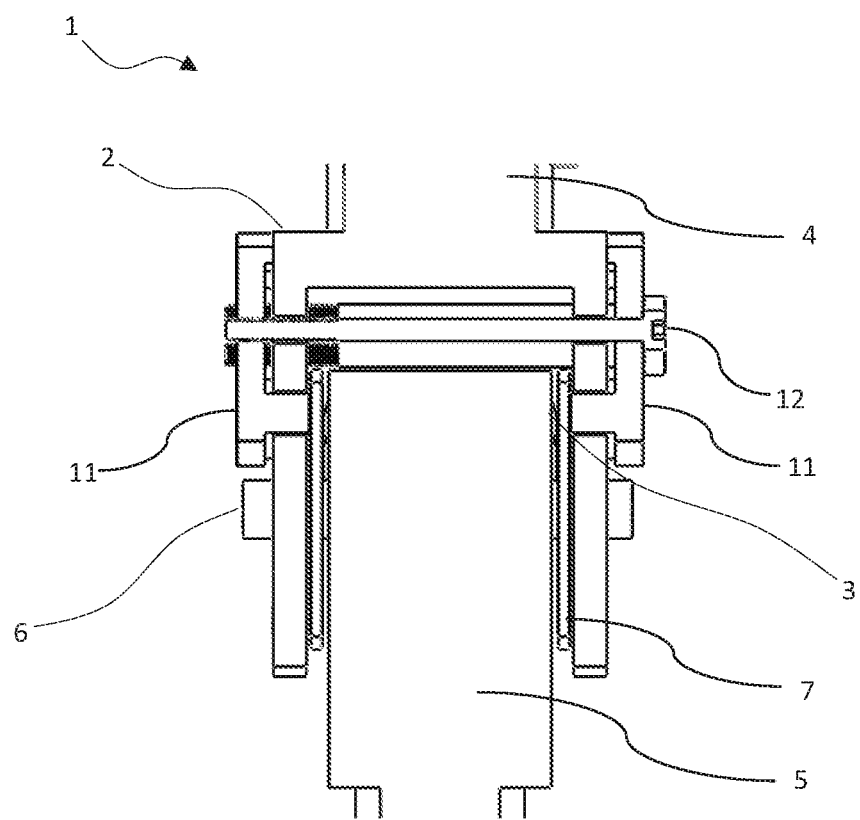
FIG. 15 is a cross-sectional view of the VFS controller of the knee joint of FIG. 14, in accordance with an example embodiment.

FIG. 15 is a cross-sectional view of the VFS controller 3 of the knee joint 2 of FIG. 14, in accordance with an example embodiment. As shown, the VFS controller 3 includes the force applicator arms 11 and friction control screws 12, as described above. Further, the artificial joint 2 includes the one or more axes 6, where the artificial joint 2 is attachable between a first limb portion 4 and a second limb portion 5, to articulate the first limb portion 4 and the second limb portion 5 around the one or more axes 6. Further, the VFS controller 3 may be configured to vary friction associated with the articulation based on an amount of the articulation around the one or more axes 6. In particular, the friction may vary with a first frictional surface of the first limb portion 4 (e.g., the friction shims 7) and a second frictional surface of the second limb portion 5. As such, the force applicator arms 11 and friction control screws 12 may be configured to apply a force on the first frictional surface and/or the second frictional surface to further vary the friction based on the amount of the articulation around the one or more axes 6.

Figure 16:
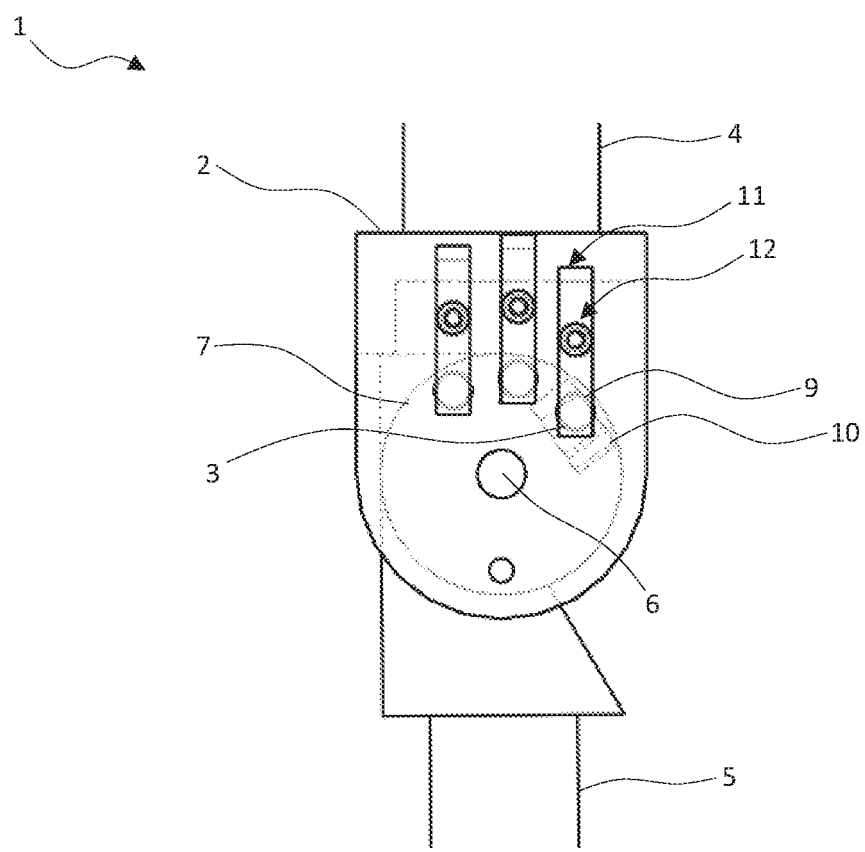
FIGS. 16 and 17 are side views of the VFS controller of the knee joint of FIG. 14 and the force applicators that may change the variable amounts of interference at variable degrees of knee flexion, in accordance with an example embodiment.
Figure 17:
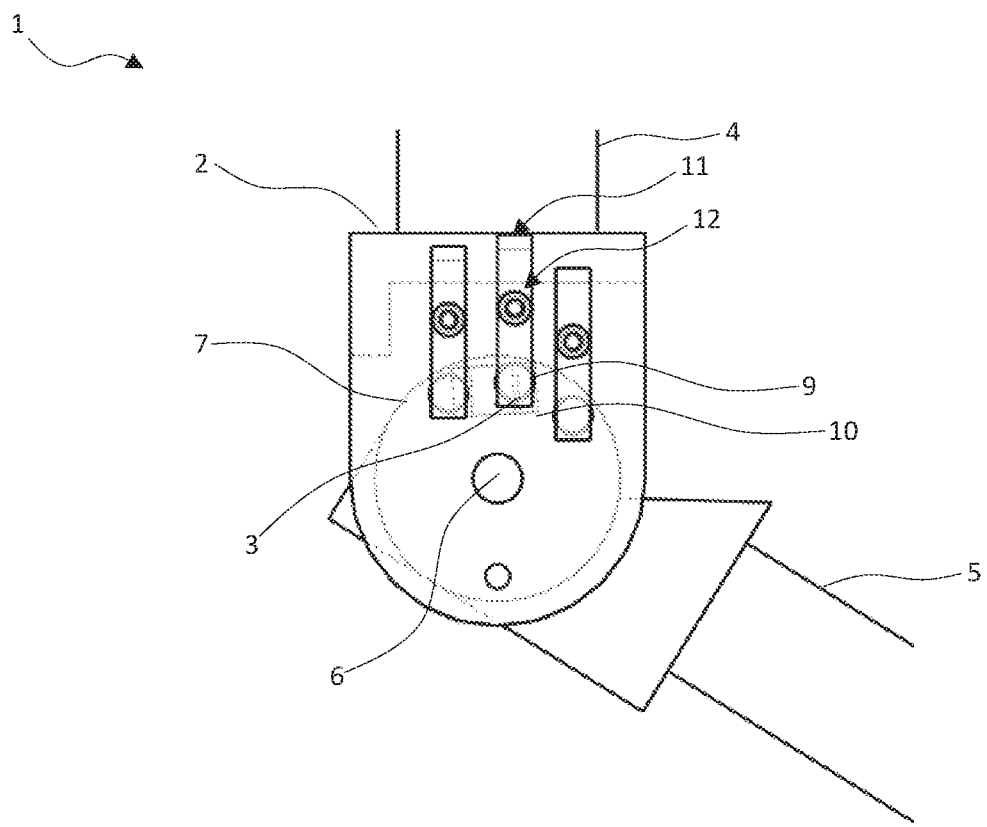

FIGS. 16 and 17 are side views of the VFS controller 3 of the knee joint 2 of FIG. 14 and the force applicators 9 and 10 that may change the variable amounts of interference at variable degrees of knee flexion, in accordance with an example embodiment. FIG. 16 illustrates the knee joint 2 in a fully extended, straight position in relation to the thigh portion 4, the one or more axes 6, and the shank portion 5. FIG. 17 illustrates the knee joint 2 in a flexed position around knee axis 6. Further, FIG. 16 provides the force applicator arms 11 and the force applicator 10 are overlapping, indicating an increase in interference resulting in an increase in force that applies frictional resistance to the swing-phase of knee joint 2. Further, FIG. 17 provides two force applicator arms 11 and the force applicator 10 overlapping, resulting in a further increase in force that is applying frictional resistance to the swing-phase of knee joint 2. This frictional resistance of the knee joint 2 provides an improvement of control associated with various levels of increased interference at different amounts of articulation or knee flexion. Notably, the friction control screw 12 may be used to adjust the force applicator arms 11, possibly based on the force applicator 9 and the friction shim 7.

Figure 18:
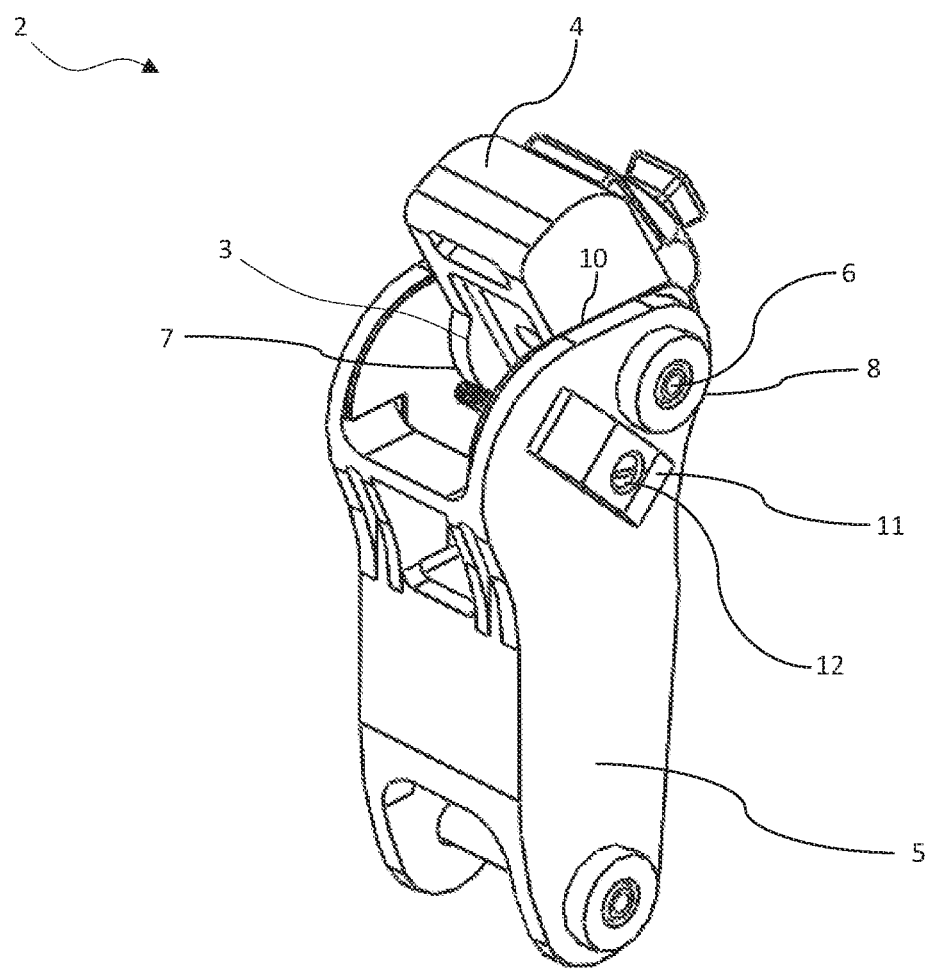
FIGS. 18 and 19 are perspective views of the VFS controller of the knee joint of FIG. 14 in the All-Terrain (AT) Knee, in accordance with an example embodiment.
Figure 19:
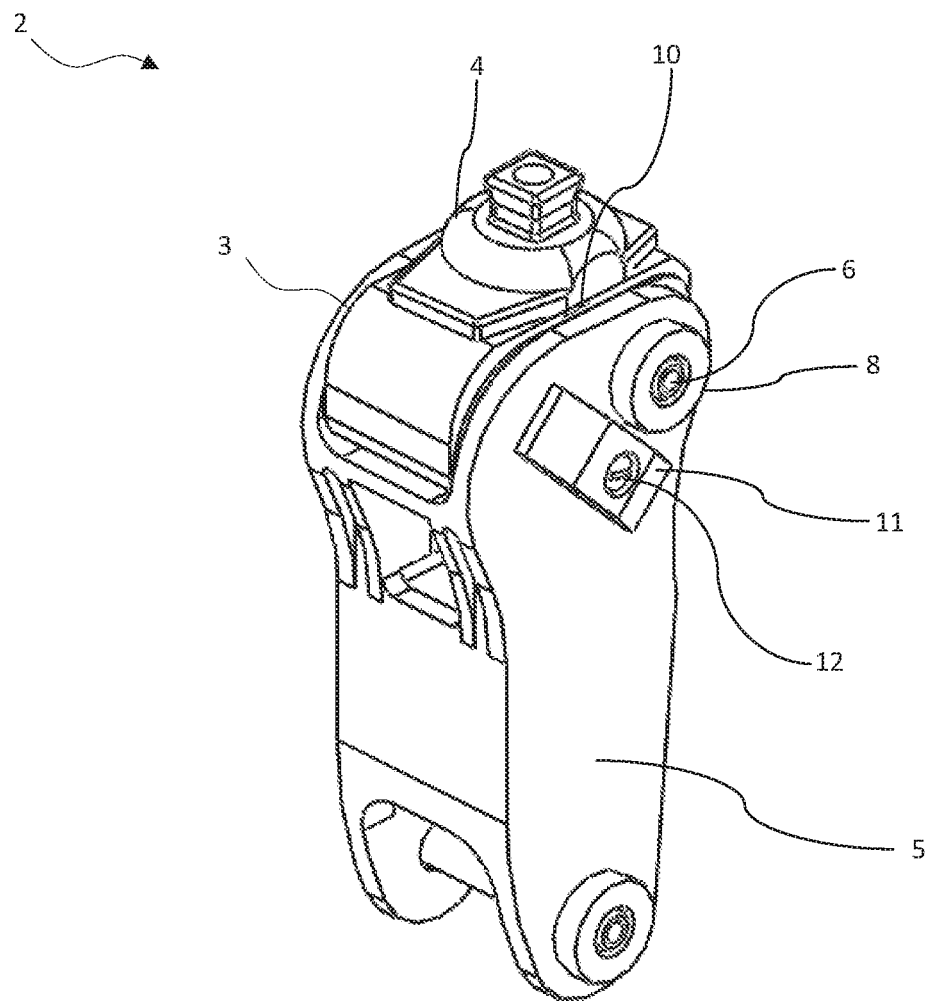

FIGS. 18 and 19 are perspective views of the VFS controller 3 of the knee joint 2 of FIG. 14 in the All-Terrain (AT) Knee, in accordance with an example embodiment. As shown, the thigh portion 4 and/or the shank portion 5 may articulate around the one or more axes 6 shown in relation to the friction control screw 8. The force applicator arm 11 and the friction control screw 12 may provide increased force and interference in relation to the lever arm length with the alteration of the overlapping surface shapes of the friction shims 7 of the shank portion 5 and the force applicator 10.

Figure 20:
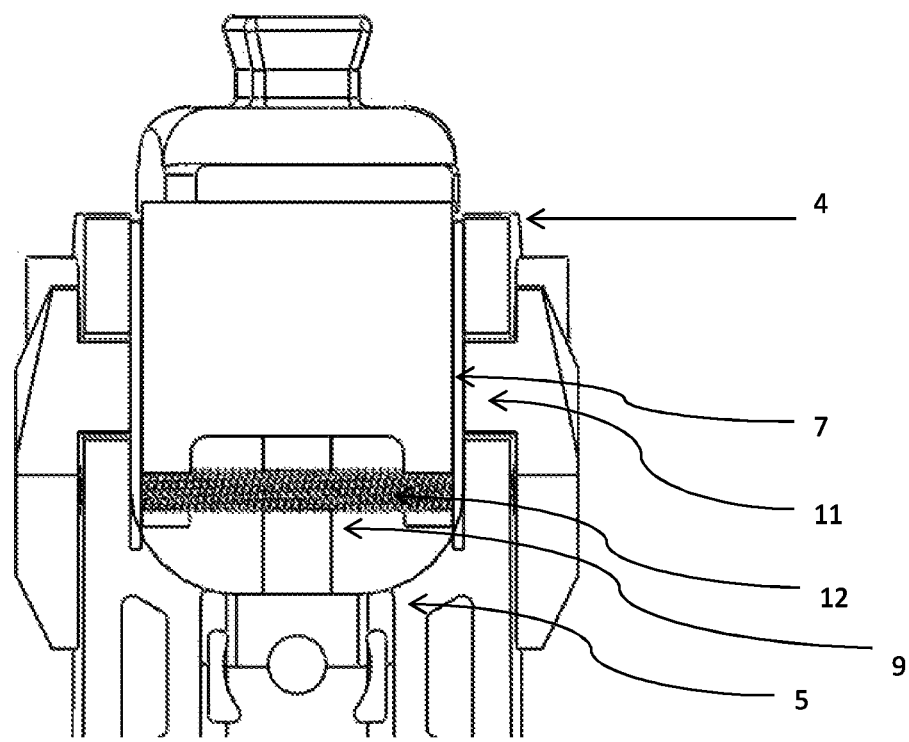
FIG. 20 is a cross-sectional view of the VFS controller of the knee joint of FIGS. 18 and 19, in accordance with an example embodiment.

FIG. 20 is a cross-sectional view of the VFS controller of the knee joint of FIGS. 18 and 19, in accordance with an example embodiment. As shown, the thigh portion 4 and/or the shank portion 5 may articulate based on the force applicator arms 11, force applicator friction control screws 12, and the friction shim 7. As further shown, a second controller 9 comprises or otherwise includes at least one of a hydraulic controller, a pneumatic controller, and extension spring(s).

Figure 21:
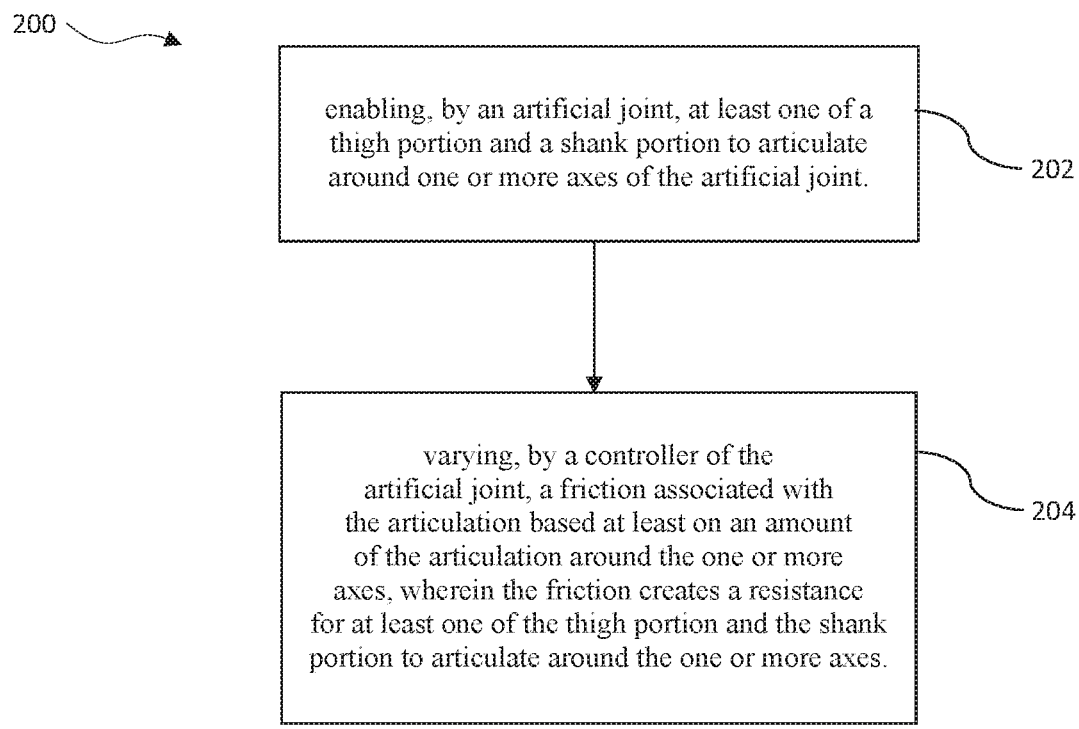
FIG. 21 is a block diagram of an example method of an artificial joint varying a friction associated with articulation based on an amount of the articulation, in accordance with an embodiment.

FIG. 21 is a block diagram of an example method of an artificial joint varying friction associated with articulation based on an amount of the articulation, in accordance with an embodiment. Method 200 presents an example method that could be performed with the artificial joint 2 described above in relation to FIGS. 1-20. Further, the method 200 may be carried out by the VFS controller 3 performing one or more steps provided in the method 200.

At step 202, the method 200 includes an artificial joint enabling at least one of a thigh portion and a shank portion to articulate around one or more axes of the artificial joint. For example, the artificial joint 1 may enable at least one of the thigh portion 4 and the shank portion 5 to articulate around one or more axes 6 of the artificial joint 1. In some instances, the artificial joint 1 may enable the thigh portion 4 and/or the shank portion 5 to articulate, pivot, and/or rotate around the one or more axes 6 by being attached to the thigh portion 4 and/or the shank portion 5, possibly with one or more components, such as the friction control screw 8.

At step 204, the method 200 includes a controller of the artificial joint varying a friction associated with the articulation based at least on an amount of the articulation around the one or more axes, where the friction creates a resistance for at least one of the thigh portion and the shank portion to articulate around the one or more axes.

Referring back to FIGS. 3-4, the VFS controller 3 includes the friction control screw 8. As such, the method 200 further includes varying the friction associated with the articulation based at least on the friction control screw 8.

Referring back to FIGS. 1-20, the VFS controller 3 includes a first frictional surface associated with the thigh portion 4 (e.g., the friction shim 7) and a second frictional surface associated with the shank portion 5. Further, the method 200 further includes varying the friction based on at least one of the first frictional surface (e.g., the friction shims 7) interacting with the second frictional surface.

Further, the VFS controller 3 may also include the lever arm described above associated with respective interacting surface areas from the first frictional surface and the second frictional surface. As such, the method 200 may also include varying one or more dimensions of the respective interacting surface areas based at least on the degree of the articulation. Further, the method 200 may include varying the friction based at least on the one or more varied dimensions of the respective interacting surface areas Further, referring back to FIGS. 8-20, the VFS controller 3 may also include the one or more force applicators 9 and 10. As such, the method 200 may also include one or more force applicators 9 and 10 applying a force on at least one of the first frictional surface and the second frictional surface. Further, the method 200 may also include varying the friction with the force applied based on at least one of the degree of articulation around the one or more axes.

It should be understood that arrangements described herein are for purposes of example only. As such, those skilled in the art will appreciate that other arrangements and other elements (e.g. machines, interfaces, functions, orders, and groupings of functions, etc.) can be used instead, and some elements may be omitted altogether according to the desired results. For example, the VFS controller 3 may also be utilized with other mechanisms and controllers, including, but not limited to: extension assist springs, ratchets, hydraulics, and pneumatics, among other possible components. Further, many of the elements that are described are functional entities that may be implemented as discrete or distributed components or in conjunction with other components, in any suitable combination and location, or other structural elements described as independent structures may be combined. The various aspects and embodiments disclosed herein are for purposes of illustration and are not intended to be limiting, with the true scope being indicated by the following claims, along with the full scope of equivalents to which such claims are entitled. It is also to be understood that the terminology used herein is for the purpose of describing particular embodiments only, and is not intended to be limiting.

What is claimed is:

1. An article of manufacture, comprising:
    an artificial joint comprising one or more axes, wherein the artificial joint is attachable between a first limb portion and a second limb portion, to articulate at least one of the first limb portion and the second limb portion around the one or more axes;
    a controller configured to apply an axial force to vary friction associated with the articulation based at least on an amount of the articulation around the one or more axes, wherein the friction is varied with a first frictional surface of the first limb portion and a second frictional surface of the second limb portion; and
    one or more force applicators configured to apply a force on at least one of the first frictional surface and the second frictional surface to further vary the friction based at least on the amount of the articulation around the one or more axes;
    wherein the controller comprises a friction control screw to vary the friction based at least on the amount of the articulation around the one or more axes,
    wherein the one or more force applicators comprises a first force applicator and a second force applicator, and
    wherein the controller is configured to apply a first force on the friction control screw with the first force applicator and a second force on the friction control screw with the second force applicator to further vary the friction based at least on the amount of articulation.

2. An article of manufacture, comprising:
    an artificial joint comprising one or more axes, wherein the artificial joint is attachable between a first limb portion and a second limb portion, to articulate at least one of the first limb portion and the second limb portion around the one or more axes;
    a controller configured to apply an axial force to vary friction associated with the articulation based at least on an amount of the articulation around the one or more axes, wherein the friction is varied with a first frictional surface of the first limb portion and a second frictional surface of the second limb portion; and
    one or more force applicators configured to apply a force on at least one of the first frictional surface and the second frictional surface to further vary the friction based at least on the amount of the articulation around the one or more axes;

wherein the controller comprises a plurality of friction control screws that correspond to a plurality of force applicator arms, wherein each friction control screw from the plurality of friction control screws is configured to apply a respective force on a corresponding force applicator arm from the plurality of force applicator arms, and wherein the controller is configured to vary the friction by applying respective forces from the plurality of friction control screws to the plurality of force applicator arms based at least on the amount of the articulation around the one or more axes.

3. The article of manufacture of claim 2, wherein the first frictional surface comprises a friction shim, and wherein the controller is configured to vary the friction based at least on the respective forces being applied to the friction shim.

4. The article of manufacture of claim 2, wherein the controller is configured to apply the respective forces based at least on each force applicator from one or more force applicators overlapping with a corresponding force applicator arm from the plurality of force applicator arms.

* * * * *